US006833139B1

(12) United States Patent
Lemko et al.

(10) Patent No.: US 6,833,139 B1
(45) Date of Patent: Dec. 21, 2004

(54) COMPOSITION AND METHOD FOR THE TREATMENT OF ANORECTAL DISORDERS

(75) Inventors: Mark Lemko, Plymouth, MI (US); Pravin M. Patel, Bloomfield Hills, MI (US)

(73) Assignee: Ferndale Laboratories, Inc., Ferndale, MI (US)

( * ) Notice: Subject to any disclaimer, the term of this patent is extended or adjusted under 35 U.S.C. 154(b) by 215 days.

(21) Appl. No.: 10/042,818

(22) Filed: Jan. 9, 2002

(51) Int. Cl.[7] ................................................ A61K 9/127
(52) U.S. Cl. ...................................... 424/450; 514/882
(58) Field of Search ........................ 424/450; 514/554, 514/631, 882

(56) References Cited

U.S. PATENT DOCUMENTS

| | | | |
|---|---|---|---|
| 4,686,211 A | * | 8/1987 | Hara |
| 4,839,175 A | | 6/1989 | Guo et al. .................. 424/450 |
| 4,849,227 A | | 7/1989 | Cho ........................... 424/498 |
| 4,937,078 A | | 6/1990 | Mezei et al. ................ 424/450 |
| 4,963,367 A | | 10/1990 | Ecanow ...................... 424/485 |
| 5,260,066 A | | 11/1993 | Wood et al. ................ 424/447 |
| 5,425,954 A | | 6/1995 | Thompson et al. .......... 424/401 |
| 5,472,706 A | | 12/1995 | Friedman et al. ............ 424/450 |
| 5,504,117 A | | 4/1996 | Gorfine ....................... 514/742 |
| 5,595,753 A | | 1/1997 | Hechtman ................... 424/436 |
| 5,693,676 A | | 12/1997 | Gorfine ....................... 514/742 |
| 5,767,106 A | | 6/1998 | Turley et al. .................. 514/54 |
| 5,827,889 A | | 10/1998 | Cunico ........................ 514/565 |
| 5,919,775 A | | 7/1999 | Amin et al. ................. 514/152 |
| 5,922,332 A | | 7/1999 | Fossel ......................... 424/401 |
| 5,981,474 A | | 11/1999 | Manning et al. ............... 514/2 |
| 6,117,877 A | | 9/2000 | Fogel .......................... 514/260 |
| 6,159,944 A | * | 12/2000 | Fogel |
| 6,287,601 B1 | | 9/2001 | Russell ....................... 424/485 |
| 6,391,869 B1 | * | 5/2002 | Parks |

* cited by examiner

*Primary Examiner*—Gollamudi S. Kishore
(74) *Attorney, Agent, or Firm*—Gifford, Krass, Groh, Sprinkle, Anderson & Citkowski, P.C.

(57) ABSTRACT

A topical preparation for the treatment of anorectal disorders comprises L arginine and a local anesthetic. The L arginine typically comprises 0.1–5% by weight of the composition, and the local anesthetic typically comprises, by weight, 1–15% of the composition. Lidocaine is particularly preferred local anesthetic. In some embodiments, the composition includes a liposomal carrier, and the local anesthetic is encapsulated within the liposomes.

13 Claims, No Drawings

COMPOSITION AND METHOD FOR THE TREATMENT OF ANORECTAL DISORDERS

FIELD OF THE INVENTION

This invention relates generally to topical compositions and methods for the treatment of disorders of the skin and mucosal membranes. More specifically, the invention relates to compositions and methods for the treatment of anorectal disorders.

BACKGROUND OF THE INVENTION

Anorectal disorders include hemorrhoids, fissures, ulcers, spasms and the like. Such disorders are quite common, and can adversely affect a patient's quality of life. In some instances, such conditions can be severe enough to be incapacitating. A variety of materials and therapies have been implemented in an attempt to treat or control anorectal disorders. In those cases where the disorders are very severe, surgery may be required; however, in many instances, such conditions can be treated, with some success, by topical preparations.

Only recently has the role of nitric oxide (NO) as a mediator of smooth muscle contraction come to be understood. In view thereof, various materials such as organic nitrates and the like have been proposed for the treatment of anorectal disorders; however, such materials have been found to be difficult to formulate; and in many instances, such materials can produce adverse side effects on a patient. L arginine has been shown to act, in vivo, to enhance or contribute to the effect of NO on smooth muscle tissue, and it is speculated that such action is a result of L arginine acting as a competitive inhibitor of compounds that block the action of NO production in vivo. Therapeutic materials based upon L arginine have been employed for the treatment of hemorrhoids and the like. In this regard, see U.S. Pat. No. 5,595,753 and U.S. Pat. No. 5,827,889. However, the effect of L arginine on smooth muscle tissue has been found to be of relatively short duration. Consequently, L arginine treatments must be repeated on a frequent basis and/or relatively large volumes of material must be applied to a patient. This requirement limits the utility of such therapies.

As will be explained in detail hereinbelow, the present invention provides an L arginine based composition for the treatment of anorectal conditions, as well as other conditions associated with skin and/or mucosal membranes, which composition has a relatively long duration of action. The compositions of the present invention are simple to prepare and use, stable on storage, and have been found to provide long lasting relief from pain and discomfort associated with anorectal disorders and the like.

BRIEF DESCRIPTION OF THE INVENTION

There is disclosed herein a topical composition which comprises, on a weight basis, 0.1–18% of L arginine and 1–15% of lidocaine. These materials are disposed in a pharmaceutically acceptable carrier. In some embodiments, the carrier includes liposomes, and in some instances the lidocaine is contained within a non-aqueous phase disposed within the liposomes. In specific embodiments, the lidocaine comprises 1–10% of the composition, and in a specifically preferred formulation, the lidocaine comprises 5% of the formulation. In some embodiments, the L arginine is typically present in an amount of 0.1–5 weight percent of the composition; in certain embodiments, it comprises 0.1–3 weight percent of the composition; and in a specifically preferred formulation, it comprises 1% of the composition. The L arginine may be present as a free base or as a salt. The composition may further include an anti-inflammatory material such as a topical corticosteroid such as hydrocortisone or a derivative thereof.

Also disclosed herein is a method for the treatment of an anorectal disorder in a patient, and the method comprises applying the topical composition of the present invention to the affected area of the patient.

DETAILED DESCRIPTION OF THE PREFERRED EMBODIMENTS

In accord with the present invention, topical compositions for the treatment of anorectal disorders, as well as other inflammations and lesions of dermal or mucosal tissue, are comprised of L arginine and a local anesthetic. It has been found that this combination of materials provides rapid and long-lasting relief for pain, irritation and itching associated with such conditions; furthermore, the compositions are effective in promoting healing of the affected tissues. While the compositions consist essentially of L arginine and the topical anesthetic, they may include further active and/or inert ingredients.

Most typically, the compositions will include a pharmaceutically acceptable carrier. The compositions may also include coloring agents, fragrances, emollients and the like. Also, the compositions may include active ingredients such as anti-inflammatory agents including topical corticosteroids and the like, as well as antiseptics or antibiotics.

The L arginine may be present as a free amino acid, or it may be present in the form of a salt or other such complex. Also, while the compositions of the present invention are described as being based on L arginine, it is to be understood that mixtures of D and L arginine may be employed in the formulation of the therapeutic material of the present invention. All percentages given herein are on the basis of weight, and the L arginine is typically present in the compositions of the present invention on a weight percent basis of 0.1–18% of the composition. One preferred compositional range comprises 0.1–5% of L arginine, and another preferred range comprises 0.1–3% L arginine. In one preferred group of compositions, the L arginine is present at approximately 1% by weight of the composition.

The compositions of the present invention also include a local anesthetic, which is typically present in an amount of 1–15% of the composition. As is known in the art, local anesthetics (also referred to as topical anesthetics) comprise a class of anesthetic agents which are capable of penetrating dermal and mucosal tissues, and which block nerve transmission. Most local anesthetic agents consist of a lipophilic group (which is often an aromatic ring), which is connected by an intermediate chain (typically including an ester or amide) to an ionizable group, which is often an amine. Among some of the preferred local anesthetics are: lidocaine, benzocaine, tetracaine, procaine, mepivacaine, bupivacaine, prilocaine, ropivacaine, etidocaine, pramoxine, diclonine, and phenacaine. These materials may be used either singly or in combination, and it is to be understood that other members of this class may be similarly employed. One specifically preferred material for the practice of the present invention comprises lidocaine. Generally, the local anesthetic will comprise 1–15% of the composition, and in a specifically preferred formulation, the local anesthetic comprises 5% by weight lidocaine.

The composition of the present invention most preferably includes a pharmaceutically acceptable carrier. In the simplest case, the carrier may comprise a solvent for the L arginine and anesthetic, and this solvent may comprise one or more of: water, alcohols, hydrocarbons and the like. The carrier may also comprise a cream, gel or lotion base. Many such carrier formulations are well known in the art and may be adapted for the practice of the present invention. The carrier may include coloring agents, fragrances, rheology control materials and the like as is known in the art.

While the advantages of the present invention are secured by the use of formulations which include the local anesthetic and L arginine, compositions may also advantageously include other materials having therapeutic efficacy. For example, the compositions may also include topical corticosteroids or other such anti-inflammatory agents. One preferred group of anti-inflammatory agents comprises hydrocortisone and its derivatives, with one specifically preferred derivative being hydrocortisone butyrate. Other therapeutically effective materials can include analgesics such as indomethacin or ibuprofen, or vasomodifying agents such as diltiazem or sildenafil. Yet other therapeutically effective materials will include piroxicam, allantoin, naproxen, and phenylephrine. All of these ingredients may be incorporated as salts, addition compounds, complexes or free molecules. The compositions of the present invention may also include antiseptic or antibiotic materials which will serve to control secondary infections. Skin softening agents and penetration enhancers may also be incorporated into the formulations of the present invention. Still other ingredients may be incorporated, and such ingredients will be apparent to one of skill in the art.

In one preferred class of compositions of the present invention, the carrier includes liposomes. As is known in the art, liposomal structures comprise vesicles having walls formed from a phospholipid or similar material. The liposomes can serve to stabilize a dispersion of an oil phase in a water phase, or vice versa. In one embodiment of the present invention, the liposomes enclose an oil phase and are dispersed in an aqueous, continuous phase; and in such embodiments, the local anesthetic is advantageously encapsulated in the liposomes, and the L arginine is in the continuous, aqueous phase.

One specific composition in accord with the present invention comprises a liposomal preparation which includes 5% lidocaine and 1% L arginine. This composition was prepared as follows. A first mixture (mixture A) was prepared from:

1.50% isopropyl myristate 3.5% propylene glycol 1.50% benzyl alcohol 0.3% vitamin E acetate 0.75% nonionic surfactant (polysorbate 80, ICI)

0.3% cholesterol 7.32% phosphatidyl choline (Phospholipion® 80H, American Lecithin Corporation)

The foregoing materials were mixed together, at a temperature of approximately 80° C. until melted. The temperature was then reduced to 70° C., and 5% lidocaine was added. Mixing was carried out at 75 rpm for approximately 10 minutes, and 31.86% water was added. Mixing was carried on for 45 minutes under reduced pressure of approximately 15 inches Hg at a temperature of approximately 54° C.

In a next step of the preparation, 1% L arginine was dissolved in 10 parts water, at room temperature of approximately 15° C. 4.0 parts propylene glycol was added to this mixture. This mixture is designated mixture B. In a further step, 0.4 part polyacrylic polymer (Carbopol® 980NF, Union Carbide Corporation) was stirred into 32.57 parts of water at room temperature. Stirring was carried on for one half hour until a lump free dispersion was achieved.

The Carbopol® dispersion was then mixed into mixture A described above. Stirring was carried on for approximately 10 minutes at 75 rpm, at a temperature of approximately 28° C. Thereafter, the arginine solution, mixture B, was added and stirring carried on at 75 rpm, under a vacuum of 24 inches HG, for one hour. This procedure produced a liposomal preparation which included 5% lidocaine and 1% L arginine, wherein the lidocaine was contained within an oil phase of a liposomal structure, and the L arginine was in the continuous, aqueous phase.

The concentration of the L arginine may be readily varied so as to adopt the composition to specific applications. Generally, concentrations below 0.1% will have a decreased effect, and are not usually preferred. Compositions including up to approximately 18% L arginine have good therapeutic effect, and may be readily implemented in accordance with the present invention.

It is to be understood that yet other preparations may be prepared in a similar manner. For example, other local anesthetics may be substituted for the lidocaine. Also, relative proportions of the materials may be varied. Yet other preparations may comprise gels, creams or lotions, and may not include any liposomal structure.

In view of the foregoing, it is to be understood that yet other modifications and variations of the present invention may be implemented. The foregoing drawings, discussion and description are illustrative of particular embodiments of the invention, but are not meant to be limitations upon the practice thereof. It is the following claims, including all equivalents, which define the scope of the invention.

What is claimed is:

1. A topical composition consisting essentially of, on a weight basis:

0.1–18% of L arginine;

1–15% of lidocaine; and a pharmaceutically acceptable carrier which includes liposomes disposed in a continuous phase; wherein said lidocaine is disposed within said liposomes, and said L arginine is in said continuous phase.

2. The composition of claim 1, wherein said lidocaine is present in a weight amount of 1–10%.

3. The composition of claim 1, wherein said lidocaine is present in a weight amount of 5%.

4. The composition of claim 1, wherein said L arginine comprises 0.1–3 weight percent of said composition.

5. The composition of claim 1, wherein said L arginine comprises, on a weight basis, 1% of said composition.

6. The composition of claim 1, wherein said L arginine is present as a salt.

7. A topical composition consisting essentially of, on a weight basis:

0.1–18% of L arginine;

1–15% of lidocaine;

a topical corticosteroid; and a pharmaceutically acceptable carrier which includes liposomes disposed in a continuous phase; and wherein said lidocaine is disposed within said liposomes, and said L arginine is in said continuous phase.

8. A topical composition consisting essentially of, on a weight basis:

0.1–18% of L arginine:

1–15% of lidocaine; and a material selected from the group consisting of: diltiazem, indomethacin, piroxicam, naproxen, ibuprofen, sildenafil, allantoin, phenylephrine, combinations of the foregoing, and salts of the foregoing.

9. A method for treating anorectal disorder in a patient, said method comprising applying to the affected area of said patient a composition consisting essentially of:

L arginine;

a local anesthetic;

a material selected from the group consisting of: diltiazem, indomethacin, piroxicam, naproxen, ibuprofen, sildenafil, allantoin, phenylephrine, a topical corticosteroid, combinations of the foregoing, and salts of the foregoing;

a pharmaceutically acceptable carrier comprising liposomes disposed in a continuous phase; and wherein, said local anesthetic is disposed within said liposomes, and said L arginine is in said continuous phase.

10. The composition of claim 7, wherein said topical corticosteroid is hydrocortisone or a derivative thereof.

11. A method for treating an anorectal disorder in a patient, said method comprising applying to the affected area of said patient a composition consisting essentially of L arginine, a local anesthetic and a pharmaceutically acceptable carrier comprising liposomes disposed in a continuous phase;

wherein, said local anesthetic is disposed within said liposomes, and said L arginine is in said continuous phase.

12. The method of claim 11, wherein said local anesthetic comprises lidocaine.

13. The method of claim 11, wherein said L arginine comprises, on a weight basis, 0.1–5% of said composition.

* * * * *